United States Patent [19]
Ott et al.

[11] Patent Number: 5,411,474
[45] Date of Patent: May 2, 1995

[54] METHOD AND APPARATUS FOR CONDITIONING INSUFFLATION GAS FOR LAPAROSCOPIC SURGERY

[75] Inventors: Douglas E. Ott, 682 Foster Rd., Macon, Ga. 31210; John F. Schaefer; Robert I. Gray, both of Macon, Ga.

[73] Assignee: Douglas E. Ott, Macon, Ga.

[21] Appl. No.: 91,658

[22] Filed: Jul. 14, 1993

[51] Int. Cl.$^6$ .............................................. A61M 37/00
[52] U.S. Cl. ...................................... 604/26; 604/54; 604/23; 128/747
[58] Field of Search ................................ 604/23-26, 604/49, 54; 128/747-748, 202.13, 202.16, 204.17, 203.16, 203.17, 203.26, 203.27, 204.13

[56] References Cited

U.S. PATENT DOCUMENTS

| | | | |
|---|---|---|---|
| 3,871,371 | 3/1975 | Weigl | 128/145.8 |
| 4,621,633 | 11/1986 | Bowles et al. | 128/203 |
| 4,825,863 | 5/1989 | Dittmar et al. | 128/203.27 |
| 5,006,109 | 4/1991 | Douglas et al. | 604/26 |
| 5,098,375 | 3/1992 | Baier | 604/23 |
| 5,139,478 | 8/1992 | Koninckx et al. | 604/26 |
| 5,148,801 | 9/1992 | Douwens et al. | 128/203.16 |
| 5,246,419 | 9/1993 | Absten | 604/26 |

OTHER PUBLICATIONS

Douglas E. Ott, "Correction of Laparoscopic Insufflation Hypothermia," *Journal of Laparoendoscopic Surgery*, 1(4);183-186 (1991).
Douglas E. Ott, "Laparoscopic Hypothermia," *Journal of Laparoendoscopic Surgery*, 1(3):127-131 (1991).
Douglas E. Ott, "Contamination via Gynecologic Endoscopy Insufflation," *Journal of Gynecologic Surgery*, 5(2):205-208 (1989).
M. Ogino et al., "Moisture-Conserving Efficiency of Condenser Humidifiers," *Aneasthesia*, 40:990-995 (1985).
Wolf D. Seufert et al., "The Liquid Barrier Filter–A New Concept To Eliminate Particulate Contaminants From Gases," *Health Physics*, 42(2);209-216 (1982).
Thomas J. Poulton et al., "Humidification of Rapidly Flowing Gas," *Critical Care Medicine*, 9(1):59-63 (1981).
P. Whitehurst et al., "Temperature Alarm and Cut-Out System for Use With Heated Water Humidifiers," *Br. J. Anaesth.*, 52:557-558 (1980).
Jack Chalon, et al., "Humidification in a Modified Circle System," *Anesth. Analg.* 58(3):216-220 (May-Jun. 1979).
G. C. Grant et al., "A New Humidifier," *Anaesth. Intens. Care*, 4(3):205-210 (Aug. 1976).
Valentin N. Dolorico, "A Safe Nonrebreathing System: Humidity, Sterility, Cost," *Current Researches*, 53(1):76-79 (1974).

*Primary Examiner*—Corrine Maglione
*Attorney, Agent, or Firm*—Needle & Rosenberg

[57] ABSTRACT

The present invention provides an apparatus for treating gas prior to its use in a medical procedure comprising a housing that receives gas from an insufflator, a chamber within the housing having a humidification means, a heating means disposed within the humidification means, a filtering means within the humidification means, a means for sensing the temperature of the heated and humidified gas, and a controlling means connected to the sensing means to maintain the temperature of the gas to a predetermined temperature. Additionally provided are methods of providing heated, humidified and filtered gas to a patient at a predetermined temperature.

15 Claims, 2 Drawing Sheets

METHOD AND APPARATUS FOR CONDITIONING INSUFFLATION GAS FOR LAPAROSCOPIC SURGERY

BACKGROUND OF THE INVENTION

1. Field of the Invention

This invention relates to altering the temperature, humidity and the presence of physical and biological contaminants of gases used to inflate body cavities prior to and during medical procedures. More specifically, it relates to a compact device for, and method of, heating, humidifying and filtering insufflation gases at a point immediately prior to passage of the gases into the patient.

2. Background Art

From the beginning of laparoscopic surgical procedures some twenty years ago, it has been assumed that the condition of gases used to inflate body cavities were physiologically and pathologically benign. While the importance and use of temperature and moisture conditioning of anesthesia gases has been well known, until recently little attention had been given to the particulate, temperature and/or humidity condition of insufflation gases used to create a pneumoperitoneum.

A commonly used insufflation gas is carbon dioxide which is typically provided as a liquid in compressed gas cylinders. The pressure in these cylinders, when at equilibrium with ambient environment of 20° C., is 57 atmospheres (5740 KPa). The carbon dioxide gas is typically provided to the surgical site at a pressure of 15 mmHg via an adjustable, throttling pressure regulator and flow controller called an insufflator. Many models of insulators are available such as the Storz Model 26012 (Karl Storz Endoscopy-America Inc., Culver City, Calif.). In general, insulators do not filter, control the temperature of or humidify the gas.

When the insufflator provides gas flows of various magnitudes, typically 1 to 10 liters per minute, it must reduce the gas pressure of the gas from the cylinder pressure from about 57 atmosphere to approximately 1 atmosphere. Such a process is called "throttling," which causes the gas to be cooled via a thermodynamic process known as Joule-Thompson cooling (see, for example, Y. A. Cengel and M. A. Boles, "Thermodynamics: An Engineering Approach," McGraw-Hill, (1988)).

With the carbon dioxide as the insufflation gas, Joule-Thompson cooling can reduce the gas temperature as much as 50° to 70° C., depending on gas mass flow rates. The fortuitous, large difference in heat capacities of the insufflator metal hardware (large) and the $CO_2$ gas stream (small) permits the gas stream to be reheated to approximately operating room ambient temperature (around 20° C.) before the gas enters the patient. In the case of large gas flows, this unplanned and uncontrolled reheating effect could be incomplete and the insufflator gas could leave the insufflator apparatus at temperatures considerably less than. the ambient temperature of approximately 20° C. In any case, insufflator gas cannot reach a temperature higher than this ambient temperature, and hence, the insufflator gas enters the patient at a temperature substantially less (at least 17° C. less) than the patient's physiological core of approximately 37° C. (Ott, D. E., J. Laparoendosc. Surg., 1:127–131 (1991)).

Newly developed insufflators and ancillary devices have recognized this problem and have attempted to correct it by adding heat to the gas stream before it enters the delivery system which directs the gas to the trocars (see, for example, Computerized High Flow Insufflator (Snowden-Pencer, Inc., Tucker, Ga.) and Flow-Therme (Wisap U.S.A., Tomball, Tex.)). This method is thermodynamically unsound because it fails to recognize the thermal-capacity mismatch between the flowing gas stream and the gas delivery system between the insufflator and the trocar incision point at the abdomen, even when the delivery system is only 6 to 10 feet of polymer tubing. In addition, this method overlooks the above heat transfer that occurs between the gas stream and the ambient temperature gas delivery tubing. Because of these thermal conditions, the temperature of any gas preheated at or in the insufflator itself will return to approximately the ambient temperature after flowing as little as four (4) feet after leaving the insufflator.

U.S. Pat. No. 5,006,109 (Douglas et al.) relocates the temperature sensor to the point of gas administration, but this relocation does not solve this problem, because as has been mentioned above, that point can be, in practice, 6 to 10 feet from any temperature controller. Such an arrangement leads, with the low flow rates typically used in these surgical methods, to "transportation lags" which render stable feedback control difficult to achieve under major, rapid flow rate changes which are typically required by these endoscopic and laparoscopic surgical procedures. Thus, the gas reaches the patient at a temperature much lower than the desirable 36° C.–38° C.

Insufflation gases typically are delivered extremely dry. In accordance with Food and Drug Administration guidelines, medical grade carbon dioxide, the most prevalent gas used for laparoscopy, contains 200 parts per million or less of water vapor. The extreme lack of moisture in the insufflation gas can lead to drying of exposed tissue surface within the abdomen, and to the possibility of adhesion formation within the peritoneal cavity Corfman, R. C., *Clinical Consultations in Obstetrics and Gynecology*, 1:41–49 (1989)). With previous insufflation systems, frequent irrigation of the peritoneal cavity was required to limit adhesion formation.

The Douglas et al. patent discloses humidifying the insufflation gas prior to administration to the patient. Its method and device to achieve this objective, however, does not allow for a number of important thermodynamic and psychrometric effects. For instance, it is not effective to thermally condition and then to humidify the gas (or visa versa) in a serial order (see, for example, Chapter 5, Psychrometrics, ASHRAE Handbook, Fundamentals, Section I, (The American Society of Heating, Refrigerating and Air Conditioning Engineers, Inc., pp. 5.1–5.10 (1981)). Because of the intrinsic nature of the dependency of water vapor pressure upon temperature, it is not possible to obtain useful levels of relative humidity and temperature with the Douglas et al. device.

It is known to filter insufflation gas to prevent inorganic particles such as metallic fillings or particles, rust, dust, and polymer particles from passing into the pneumoperitoneum (se, e.g., Ott, D. E., J. Gynecol. Surg., 5:205–208 (1989)). The location and type of filter, however, are very important factors which will influence the effectiveness of the method. Filters having a pore size as small as 0.2 microns have been used in previous insufflation systems. These devices, however, utilize a filter material that is typically hydrophilic and when it becomes moist, loses its strength and some of its filtering effectiveness. These filters, because they are not hydrophobic, can lose their filtering capability by tearing under the water pressure caused by accidentally suctioning peritoneal or irrigation fluids.

Typically, insufflators and other prior art insufflation gas conditioning methods utilize conventional, 120 volt, alternating current power commonly available in all operating rooms. There are two disadvantages to this power source: The number of devices requiring such power during surgery has become very large in recent years, which reduces space near the operating table and creates a tangle of power cords which compete for outlets and sometimes interfere with operating room procedures. Secondly, despite advanced grounding and isolation device and hospital procedures, there remains a finite probability of accidentally causing dangerous, sometimes lethal, patient shock from the 120 AC voltage.

Thus, previous devices attempting to provide conditioned gas to a patient have had significant problems and limitations. Accordingly, there is a great need for a method and apparatus for the conditioning of insufflation gas with appropriate physiological temperature, humidity and purity suitable for direct introduction to the peritoneal cavity in a manner which overcomes the limitations of previous systems.

SUMMARY OF THE INVENTION

The disadvantages of the prior art are overcome by the present invention which provides a high-efficiency apparatus for heating, humidifying and filtering gas, thus allowing the gas to be delivered to the patient at an accurate temperature while also properly humidified and filtered and without the use of AC voltage. The present invention provides an efficient, compact means of providing heated and humidified gas to a patient such that heat loss in transfer of the gas is minimized, and thus, the gas is actually delivered to the patient within a desired predetermined temperature range.

Thus, a principle general object of the present invention is to provide a compact, high efficiency, lightweight apparatus for heating and humidifying gas from a commercial insufflator that can be positioned immediately adjacent to the patient so that the gas exiting the apparatus is immediately delivered into the body cavity of the patient, and that has an efficient means for simultaneously heating the gas to a predetermined, preset temperature and humidifying the gas.

The present invention provides an apparatus for treating gas prior to the use of the gas in a medical procedure involving a patient, the gas being received into the apparatus from an insufflator which receives gas from a gas source, and the gas exiting the apparatus being in flow communication with a means for delivering the gas to the interior of the patient, wherein the gas is pressure- and volumetric flow rate-controlled by the insufflator, comprising a housing having an inlet and an outlet; means for communicating the outlet of the insufflator with the inlet of the housing; a chamber within the housing and having an entry port and an exit port, the entry port of the chamber being in flow communication with the inlet of the housing; a humidification means in the chamber that is in the path of travel of the gas through the chamber; heating means disposed within the humidification means for heating the gas to a predetermined temperature; means in the housing adjacent the exit port of the chamber for sensing the temperature of the gas; and means connected to the sensing means for controlling the heating means, whereby upon the determination by the sensing means of the temperature of the gas being at a predetermined level, the controlling means regulates the amount of heat applied by the heating means to the gas within the chamber. Additionally provided is a source of power for the controlling means. Also provided is the above apparatus wherein the source of power is a battery.

Another object of the invention is to provide an apparatus having a chamber having a high efficiency humidification bed and that simultaneously provides a filtration for the gas, wherein also the heating means is disposed within the humidification means. Accordingly, the apparatus of the present invention provides for heating and humidifying gas for use in a medical procedure, comprising a chamber having an entry port and an exit port; humidification means within the chamber that is in the path of travel of the gas through the chamber; and means disposed within the humidification means for heating the gas to a predetermined temperature. The humidification means can comprise a volume of water and have the heating means disposed within or around the water.

A further object of the present invention is to provide an apparatus further having a second means in the chamber for filtering the heated and humidified gas.

Still another object of the present invention is to provide methods for delivering gas to a patient that has been humidified and heated to a predetermined temperature such that the patient receives gas that is within 2° C. of the predetermined temperature.

DESCRIPTION OF THE PREFERRED EMBODIMENTS

The present invention may be understood more readily by reference to the following detailed description of specific embodiments and the Examples and Figures included therein. Referring now to the drawings, it will become apparent that the important features of the present invention include the provision of a method and high efficiency, lightweight apparatus for heating, humidifying and filtering gas prior to delivery to a patient such that the gas reaches the patient within 2° C. of a predetermined temperature.

The present invention provides an apparatus for treating gas prior to the use of the gas in a medical procedure involving a patient, the gas being received into the apparatus from an insufflator which receives gas from a gas source, and the gas exiting the apparatus being in flow communication with a means for delivering the gas to the interior of the patient, wherein the gas is pressure- and volumetric flow rate-controlled by the insufflator, comprising a housing having an inlet and an outlet; means for communicating the outlet of the insufflator with the inlet of the housing; a chamber within the housing and having an entry port and an exit port, the entry port of the chamber being in flow communication with the inlet of the housing; a humidification means in the chamber that is in the path of travel of the gas through the chamber; heating means disposed within the humidification means for heating the gas to a predetermined temperature; means in the housing adjacent the exit port of the chamber for sensing the temperature of the gas; and means connected to the sensing means for controlling the heating means, whereby upon the determination by the sensing means of the temperature of the gas being at a predetermined level, the controlling means regulates the amount of heat applied by the heating means to the gas within the chamber. Additionally provided is a source of power for the controlling means. Also provided is the above apparatus wherein the source of power is a battery.

As used in the claims, "a" can mean one or more.

As used herein, "a predetermined temperature" is one that has been preset and is not altered during a procedure. For laparoscopic procedures, the desireable predetermined temperature is physiological body temperature, i.e, approximately 36°–38° C.

As used herein, any apparatus "immediately adjacent" to a patient or an object indicates a position sufficiently physically dose in proximity to the patient or object such that gas at a temperature in the apparatus will not lose more than 2° C. while traveling from the apparatus to the interior of the patient or object. Such a distance would be, for example, from about 0–10 inches, preferably from 0 to 10 cm, and more preferably from 0 to 3 cm. Thus, the heater itself, within the chamber of the apparatus, is immediately adjacent to the patient.

Figures 1, 2:
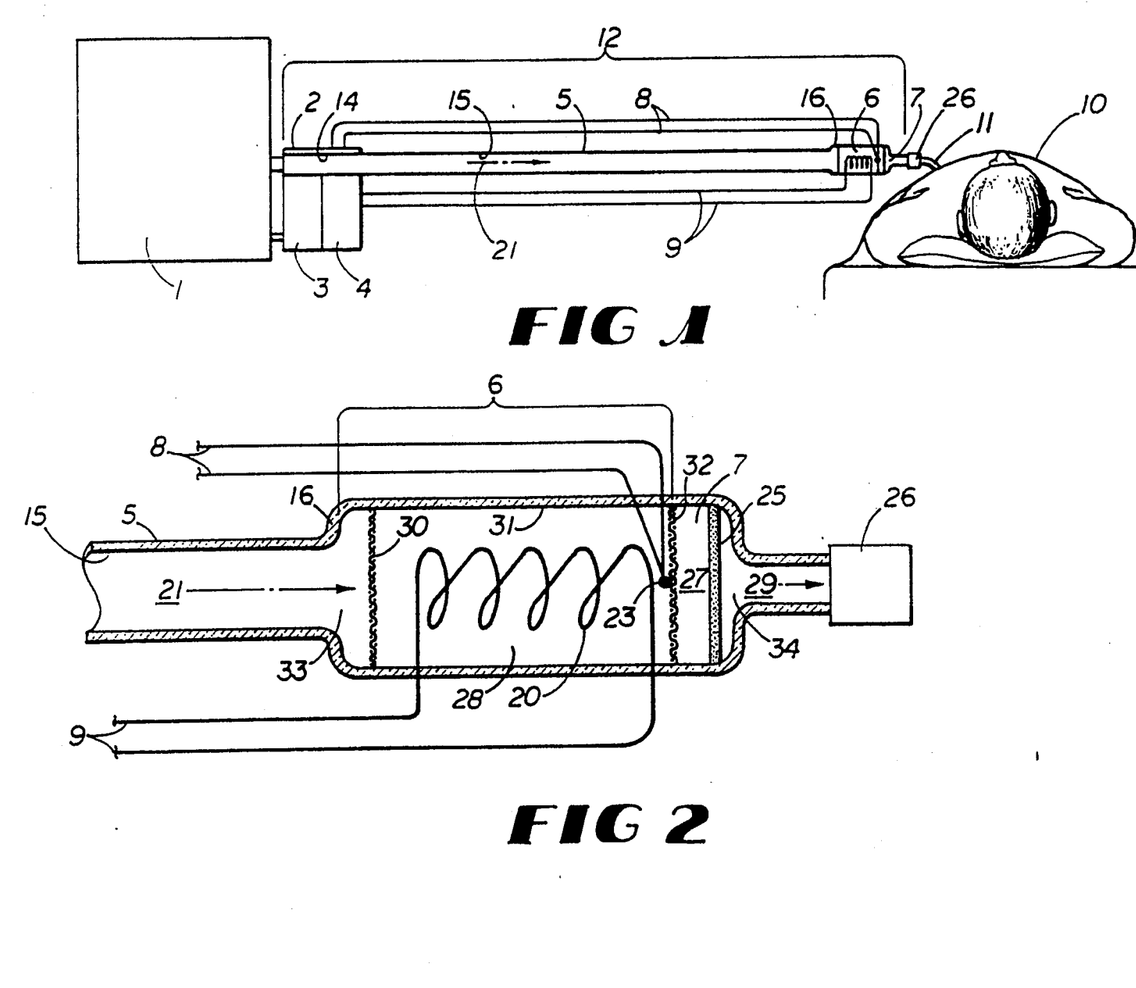
FIG. 1 is a schematic view of a gas treatment apparatus embodying the present invention, the apparatus being connected to an insufflator at one end and a means for delivering the gas to a patient at the opposite end, and being broken away at the heating and humidifying chamber to show the heating element within the chamber.
FIG. 2 is a cross-sectional view of the heating and humidifying chamber of the present invention.

A system for conditioning gas embodying the various features of the invention is illustrated in FIG. 1, in which a patient 10 is shown lying on a bed or other support at a distance from a commercially available insufflator 1 (e.g., Storz Model 26012) which receives gas from a source such as a cylinder (not shown). The apparatus 11 of the present invention is located between the insufflator 1 and a gas delivery device 11, such as a trocar or a needle, inserted into patient 10, in flow communication with both the insufflator 1 and the patient 10.

FIG. 1 illustrates a simplified version of the apparatus of the present invention. The insufflator 1 is closely connected to an optional container 2, which serves to enclose a battery power supply 3, and an electronic temperature control circuit 4 (see FIG. 3). A preferred embodiment provides for the power to be activated automatically by the attachment of container 2 to insufflator 1, such that heating can begin prior to activation of insufflator 1. An optional interior passage 14 within container 2 permits gas 21, which is pressure and flow regulated by insufflator 1, to pass through it and into a lumen 15 of a gas transfer tube 5 which is connected to housing 16 such that lumen 15 is in flow communication with chamber 6. In an alternative embodiment, interior passage 14 can be designed to loop into control circuit 4 within container 2 before flowing into gas transfer tube S. Such an arrangement allows heat exchange to occur between the relatively cool gas 21 within interior passage 14 and the relatively warm control circuit 4, thereby cooling control circuit 4 and preheating gas 21. In this alternative embodiment, interior passage 14 passes proximal enough to control circuit 4 to allow heat exchange to occur.

The gas transfer tube 5 is preferably flexible and sufficiently long to permit the insufflator 1 and power supply 3 and control circuit 4 within container 2 to be placed at a convenient distance from the patient 10 undergoing laparoscopic or other surgery while housing 16 can be placed immediately adjacent to the patient 10. Gas delivery device 11, which inserts into patient 10, preferably does not cause the gas to travel more than about 10 inches, more preferably not more than about 10 centimeters, and preferably between about 0 and 3 centimeters, from housing 16, before it reaches the interior of patient 10. The purpose of this arrangement is to allow gas to be delivered to the patient 10 while still at a temperature sufficiently close to physiological interior body temperature. That is, the invention prevents thermodynamic cooling of medical gases in transit to the patient, because it provides a highly efficient heating and humidifying chamber 6 that, because of its efficiency, can be quite compact and thus be positioned very near to patient 10. In a preferred embodiment, heater/humidification chamber 6 is so compact and lightweight that the operator can hold chamber 6 to deliver gas. The gas transfer tube 5 and chamber 6 can be reused but are preferably disposed after single usage.

Once the insufflator 1 is activated, it receives gas from the gas supply cylinder and regulates the pressure and flow rate of the gas, both of which can be adjusted by the operator. Insufflator gas 21 then flows the full length of transfer tube 5 within lumen 15 where it enters heater/humidification chamber 6 at entry port 33, crosses optional gas permeable membrane 30 and enters enclosure 31, where it comes into contact with electrical heating element 20 and water-containing humidifying bed 28, shown in FIG. 2. The pressure and volumetric flow rate are controlled by adjusting the insufflator controls (not shown). In chamber 6, insufflator gas 21 is simultaneously heated and humidified to the proper physiological range by regulation of heater element 20 such that the temperature of gas 27 exiting chamber 6 is within a preselected physiological temperature range (preferably 36° to 38° C., through any desired temperature range can be preselected). The water-containing humidifying bed 28 provides humidification within chamber 6 such that gas 27 exiting chamber 6 is humidified. After the insufflator gas 21 has been temperature/humidity conditioned in chamber 6, it exits enclosure 31 (as gas 27) through optional gas permeable membrane 32, and enters chamber 7 where it passes through a high efficiency filter 25. The gas 27 then exits chamber 7 through exit port 34 (as gas 29) and into connector 26, which can attach to a conventional gas delivery device 11 appropriate for the specific medical procedure for immediate delivery of gas 29 into patient 10.

The heater element 20 of the heater/humidification chamber 6 receives its power from the battery power supply 3 and control circuit 4 by a flexible power wire pair 9 which can be attached to the outside, or be embedded within, the wall of the gas transfer tube 5. Alternatively, gas transfer tube 5 can be provided with an additional lumen through which power wire pair 9 can pass.

Feedback temperature regulation of the heater/humidification chamber 6 is accomplished by detecting the temperature of gas 21 at the exit end of enclosure 31 by temperature sensing device 23 and transferring the signal representing this temperature by signal transfer wire pair 8 to control circuit 4 of container 2. As with power wire pair 9, signal transfer wire pair 8 can be attached to the outside, or be embedded within, the wall of gas transfer tube 5, or gas transfer tube 5 can be provided with an additional through which signal transfer wire pair 8 can pass.

Figure 3:
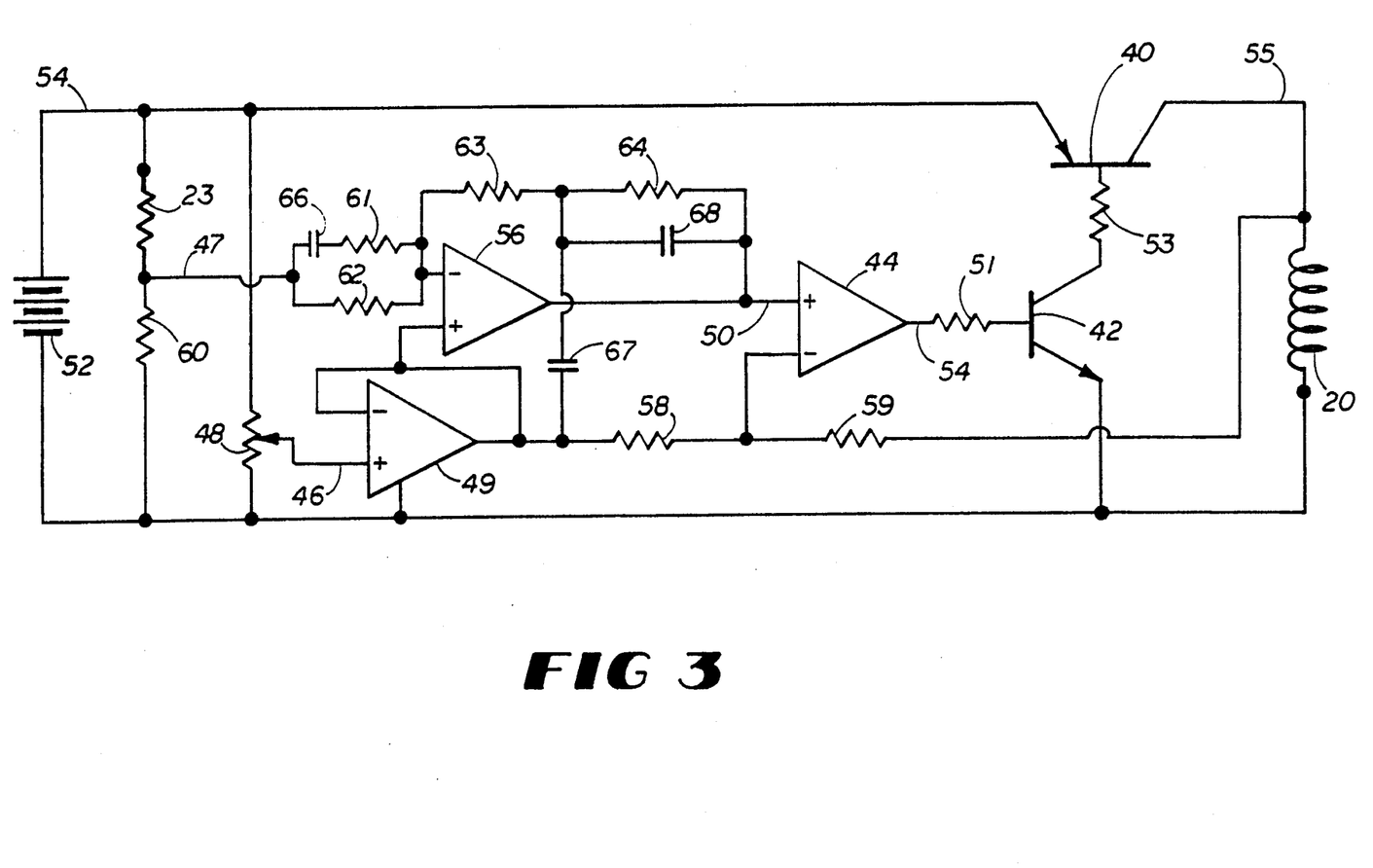
FIG. 3 is a typical wiring schematic of the means for sensing the temperature within the chamber and controlling the heating element within the chamber.

The temperature control circuit 4 is shown in detail in FIG. 3. The circuit 4 is powered by batteries 52 of battery power supply 3 located in container 2 and provide the circuit with a battery voltage 54. The use of a low voltage DC power source in this invention enables the apparatus to be independent of conventional AC electrical wiring of the hospital or clinic where the laparoscopic or other medical procedure is being carried out, which results in simple and quick installations and reduced wire clutter in the neighborhood of the surgery. Additionally, such low voltage DC power assures that the invention will be intrinsically safe from accidentally delivering dangerous electrical shocks to the patient or healthcare personnel. A self-contained battery having a voltage of from about 1.6 to about 3.0 V is preferred, with a battery having voltage of from about 2.6 to about 3.0 V being even more preferred (for example, Ray-o-Vac D cell, Ray-o-Vac Corp. Madison, Wis.).

Optimal temperature of gas 29 that enters patient 10 is at or near physiological interior body temperature (i.e., approximately 36° C. to 38° C.), or within 2° C. of physiological body temperature, or even more preferably, within 0.5° C. thereof. The temperature of the heated and humidified gas 27 is detected by a temperature sensing device 23. As the temperature of temperature sensing device 23 changes, so does its electrical resistance, which in turn causes the current flow through it and resistor 60 to change, and therefore, the sense voltage 47 (V47) to be altered according to the proportion of the resistance of temperature sensor 23 to the total of the resistance of temperature sensor 23 plus that of resistor 60.

Power transistor 40 (for example, MJE 2955, Motorola, Phoenix, Ariz.) controls the time average voltage across electrical heater element 20. Power transistor 40 is itself controlled by transistor 42, whose base current is determined by the output voltage of the operational amplifier 44 (for example LM358, National Semiconductor, Inc., Santa Clara, Calif.). The operational amplifier 44, resistors 51, 53, 58, 59, heater element 20, and transistors 40 and 42 function as an inner feedback loop such that heater voltage 55 (V55) is given by: $V55 = V50 + (R59/R58)(V50 - V46)$, wherein V50 is voltage 50, R59 is resistance at resistor 59 and R58 is resistance at resistor 58. Variable potentiometer 48 provides the variable set point of the temperature controller and generates the variable reference voltage 46 (V46), which has a value between zero and battery voltage 54. Operational amplifier 49 is a unity gain buffer which insures the voltage 46 is independent of other circuit variables.

The sense voltage 47 (V47) and the reference voltage 46 (V46) are inputs to operational amplifier 56, which in turn outputs a voltage 50 (V50). Operational amplifier 56, resistors 61, 62, 63 and 64 and capacitors 66, 67 and 68 act as two lead compensation networks to ensure a stable feedback system. The effect of this circuit is to cause the heater element voltage 55, at zero frequency, to be given by: $V55 = V46 + (1 + R59/R58)((R63 + R64)/R62)(V47 - V46)$, wherein R63, R64 and R62 are resistance at resistor 63, 64 and 62, respectively.

The location of container 2 in this preferred embodiment was selected to use the insufflator for access convenience and for physical support. Since no gas processing occurs in container 2, the existence and location of container 2 is arbitrary and, if it is used, it can be placed at any position along gas transfer tube 5. If container 2 is not used, battery power supply 3 and control circuit 4 can be placed at any convenient point(s) along gas transfer tube 5.

FIG. 2 gives the specific configuration of the heating-/humidification method and chambers 6 and 7. Insufflator gas 21 enters chamber 6 from lumen 15 through entry port 33. Gas 21 then crosses optional gas permeable membrane 30 to enter enclosure 31, which contains a humidification bed 28 comprising a porous bed or reservoir of entrapped water, the water preferably being sterile. Humidification bed 28 is preferably composed of a water-retaining material which has been infused with water. The material can be any desireable water-retaining material, preferably a borosilicate-type material (e.g., Type A/E Glass Fiber Filters or Extra Thick Glass Fiber Filters, Gelman Sciences, Ann Arbor, Mich.). The pore size of the selected material should be chosen according to a balance of water retention capabilities and filtering capabilities. The larger the pore size, the more water retention for humidification. However, in some embodiments, humidification bed 28 also serves to filter gas 21, and the pore size chosen will depend upon the adequacy of filtration desired, as well as the presence or absence of filter 25 in chamber 7. In the presence of filter 25 in the apparatus, the pore size of the material of humidification bed 28 can be chosen for water retention capabilities only, e.g., about 1 micron. Furthermore, when a water-retaining material infused with water comprises humidification bed 28, gas permeable membranes 30 and 32 are not necessary.

Embedded in humidification bed 28 is an electric resistance heater element 20 which heats humidification bed 28 to a temperature that is predetermined, i.e., preset within control circuit 4. Electric current is supplied to the heater element 20 via power wire pair 9, from battery power supply 3 located in container 2. A temperature sensing device 23, such as a thermistor (for example, Thermometrics Series BR23, Thermometrics, Inc., Edison, N.J.), is located just prior to or immediately after optional gas permeable membrane 32 to sense the temperature of gas 21 as it exits enclosure 31, and is used to generate a temperature indicating signal which is transferred to the feedback control circuit 4 via signal transfer wire pair 8. It is preferable that the temperature sensor 23 be accurate to within about 0.1 ° C. It is vital to the present invention that the temperature is sensed after it has been humidified so that any change in the temperature of gas 21 as it is humidified is corrected at that point in the apparatus. Details of power supply 3 and electronic control circuit 4 are shown in FIG. 3. A preferred range of humidification is from about 85-98% humidity.

The temperature- and humidity-conditioned gas 27 enters chamber 7, wherein it passes through an optional high efficiency, hydrophobic filter 25 (for example Gelman Sciences Metrical M5PU025) having a pore size preferably small enough to exclude all solid particles and bacterial or fungal agents that may have been generated in the gas supply cylinder, insufflator 1, or any location in the invention, including heater/humidifier bed 28 (i.e., 0.5 micron or less and preferably about 0.3 micron). A preferable filter is a hydrophobic filter, such as a glass fiber-type filter, e.g., Metrigard (Gelman Sciences). Other suitable filters include polysulfone (Supor, HT Tuffrin, Gelman Sciences) and mixed cellulose esters (GN-6Metrical, Gelman Sciences), for example. Decreasing the pore size of filter 25 below 0.3 micron causes a concomitant increase in pressure drop of gas 29, and thus flow rate is reduced significantly. If the medical procedure to be performed requires a relatively high pressure and/or flow rate of gas to the patient, such as laparoscopy, filter 25 pore size should preferably not decrease below 0.3 micron. The diameter of filter 25 should be chosen to fill the width of chamber 7 such that all gas passes through filter 25. A hydrophobic filter is preferable to a hydrophilic one, as a hydrophobic filter is less likely to tear under water pressure caused by accidentally suctioning peritoneal or irrigation fluids.

The filtered and temperature/humidity conditioned gas 29 passes directly to a connector 26, designed to attach to a conventional trocar used to inflate the peritonea or other such gas delivery device for the particular medical procedure. Housing 16 is preferably placed such that exit port 34 is within about 0 to 10 inches preferably within about 0 to 10 centimeters from patient 10, and more preferably within about 1 to 3 centimeters. Thus, the gas 29 that is now heated, humidified and filtered passes immediately into the delivery device 11 and into the interior of patient 10, while still maintained at the desired temperature, or at least within about 2° C. of it, and preferably within about 0.5° C., because the invention is of such high efficiency and is designed to allow the heating to occur just proximal to the patient.

The length and width of chamber 6 can be varied such that proper heating and humidification still occur. As an example, an average chamber 6 will contain from about 3 to about 6 cubic centimeters of water, and it is desireable that gas have a dwell time within the chamber of at least approximately 0.01 to 0.5 second. Thus, the desireable width and diameter of the chamber will also be dependent upon the rate of gas flow from insufflator 1, which is usually from about 1–10 liters/minute, and upon the pressure desired to be maintained, which is affected more by diameter of chamber 6 than by length. A person of skill in the art, given the teachings and examples herein, can readily determine useful dimensions for chamber 6 without undue experimentation. It should also be noted, however, that upon activating the apparatus or changing the demand on the apparatus (e.g., flow rate or pressure), there is a lag time of milliseconds for sensing the temperature of gas and adjusting the heating to achieve the proper gas temperature. Such a fast start-up time is extremely beneficial. Furthermore, approximately the first 12 to 15 cubic centimeters of gas leaving the apparatus after it is activated are cooler than the predetermined temperature.

The apparatus of the present invention provides for heating and humidifying gas for use in a medical procedure, comprising a chamber having an entry port and an exit port; humidification means within the chamber that is in the path of travel of the gas through the chamber; and means disposed within the humidification means for heating the gas to a predetermined temperature. The humidification means can comprise a volume of water and have the heating means disposed within or around the water, as described above. The water can be contained within water-retaining material such as a borosilicate-type material, as described above. Additionally, a filtering means can be provided, by the humidification bed and/or by an additional filter within the chamber. Filter sizes are preferably as described above.

The present invention also provides a method of providing heated, humidified gas into a patient for an endoscopic procedure comprising the steps of directing pressure- and volumetric flow rate-controlled gas, received from an insufflator into a chamber having a means for heating the gas to a temperature within a predetermined range and a means for humidifying the gas and being disposed immediately adjacent to the patient, wherein the chamber is in flow communication with and immediately adjacent to a means for delivering the gas to the interior of the patient; sensing the temperature of the gas as it exits the chamber to determine if it is within the predetermined range; and actuating the heating means if the temperature of the gas is without the predetermined range; humidifying the gas within the chamber; and flowing the gas into the delivering means such that the gas enters the patient humidified and having a temperature within 2° C. of the predetermined temperature and thus providing the gas. The heating means and the humidifying means can heat and humidify the gas simultaneously. The gas can be filtered as described above, as the gas is heated and humidified and/or immediately after it is heated and humidified. The heating means can be controlled by a power source comprising a self-contained battery of voltage in the range of about 1.6–3.0 V. An even more preferable range is about 2.6–3.0 V.

Also provided by the present invention is a method of treating gas for use in a medical procedure comprising the steps of directing the gas into the inlet of a chamber having an inlet and an outlet and having a means for heating the gas to a temperature within a predetermined range and a means for humidifying the gas, such that the gas can be heated and humidified simultaneously; sensing the temperature of the gas as it exits the chamber to determine if it is within the predetermined range; and actuating the heating means if the temperature of the gas is without the predetermined range; humidifying the gas within the chamber; and receiving the heated and humidified gas at the predetermined temperature from the outlet of the chamber, thus treating the gas. The humidifying means can serve also to filter the gas, such as by water and/or by a water-retaining material containing water, as described above. Additionally, the heated and humidified gas can be filtered a second time through a second filter within the chamber.

The method and apparatus of this invention can be utilized for many medical procedures requiring the provision of heated and humidified gas. The optional filtration may also be utilized according to the sterility of gas required for the procedure. The gas is chosen according to the procedure to be performed and can be any medically useful gas, such as carbon dioxide, oxygen, nitrous oxide, argon, helium, nitrogen and room air and other inert gases. Preferable gases for endoscopy are carbon dioxide and nitrous oxide. A combination of the above gases can also be used, i.e., 100% of a single gas need not be used. The procedure is preferably endoscopy such as laparoscopy, colonoscopy, gastroscopy, bronchoscopy, and thoracoscopy. However, it may also be utilized for providing heated and humidified oxygen for breathing, for example, or to administer anesthesia. In particular, the compact size of the apparatus and its use of a battery as a source of power make the invention portable and thus suitable for uses requiring portability. The gas delivery device that provides the direct contact to the patient should be selected according to the medical procedure to be performed as known to those skilled in the art.

The present invention is more particularly described in the following examples which are intended as illustrative only since numerous modifications and variations therein will be apparent to those skilled in the art.

EXAMPLES

The following table gives the temperature and humidification levels resulting from three different heater elements, and water retention porous bed sizes. Many other configurations and combinations have been tested and found satisfactory.

TABLE 1

| Porous Bed Characteristics (1) | | Operating Characteristics | | | |
|---|---|---|---|---|---|
| Size | Material | Heater Element Type (2) | Flow Rate L/m | Relative Humidity Range % (3) | Temperature Range °C. (4) |
| 3 × 16 | AT4 | 1–19L | 1.5 | 75–82 | 24–48 |
| | | | 9.0 | | 24–36 |
| 2 × 8.6 | AT4 | 0.8–15S | 1.0 | 60–70 | 22–45 |
| | | | 5.0 | 27–69 | 20–35 |
| 1.6 × 19 | GS A/D | 0.8–15S | 1.0 | 75–85 | 30–40 |
| | | | 9.0 | 85–95 | 24–32 |

(1) Size: 1st number = bed length in cm, 2nd number = bed diameter in mm. Material: Manufacturer's code: AT4, Arbor Tech, Inc., Ann Arbor, Michigan and GS A/D, Gelman Sciences, Ann Arbor, Michigan.
(2) Type: 1st number = element resistance in ohms, 2nd number = wire length in cm. Letter = L designates longitudinal, S designates spiral.
(3) Relative humidity was dependent upon selected temperature of the gas and selected gas flow rate and was not independently controlled.
(4) The listed temperatures indicate the range of temperatures from which the predetermined temperature was selected. Each selected temperature was maintained within ± 2.0° C., except for the short transient time period after start up of the apparatus or a new gas flow rate demand was placed upon the apparatus.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. An apparatus for treating gas prior to the use of the gas in a medical procedure involving a patient, the gas being received into the apparatus from an insufflator which receives gas from a gas source, and the gas exiting the apparatus being in flow communication with a means for delivering the gas to the interior of the patient, wherein the gas is pressure- and volumetric flow rate-controlled by the insufflator, comprising:
    a) a housing having an inlet and an outlet;
    b) means for communicating the outlet of the insufflator with the inlet of the housing, wherein a portion of the communicating means is positioned proximal to the controlling means, whereby the gas cools the controlling means and the controlling means preheats the gas;
    c) a chamber within the housing and having an entry port and an exit port, the entry port of the chamber being in flow communication with the inlet of the housing;
    d) a humidification means in the chamber that is in the path of travel of the gas through the chamber;
    e) heating means disposed within the humidification means for heating the gas to a predetermined temperature;
    f) means in the housing adjacent the exit port of the chamber for sensing the temperature of the gas; and
    g) means connected to the sensing means for controlling the heating means, whereby upon the determination by the sensing means of the temperature of the gas being at a predetermined level, the controlling means regulates the amount of heat applied by the heating means to the gas within the chamber.

2. The apparatus of claim 1, and further comprising a source of power for the controlling means.

3. The apparatus of claim 2, wherein the source of power is a battery.

4. The apparatus of claim 3, wherein the battery has a voltage of from about 1.6 to 3.0 volts.

5. The apparatus of claim 1, wherein the humidification means comprises a volume of water in flow communication with the gas as it travels through the chamber and having the heating means disposed within or around the water.

6. The apparatus of claim 1, and further comprising a means within the housing for filtering the gas, the filtering means being in flow communication with the exit port of the chamber.

7. The apparatus of claim 6, and further comprising a second filter positioned within and containing the water in the chamber.

8. The apparatus of claim 1, wherein the communicating means is of sufficient length to allow the housing to be disposed distal to the insufflator and proximal to the patient.

9. The apparatus of claim 8, wherein the housing is disposed within about 0 to about 10 centimeters proximal to the patient.

10. The apparatus of claim 1, wherein the medical procedure is endoscopy selected from the group consisting of laparoscopy, colonoscopy, gastroscopy, bronchoscopy and thoracoscopy.

11. A method of providing heated, humidified gas into a patient for an endoscopic procedure comprising the steps of:
    a) directing pressure- and volumetric flow rate-controlled gas, received from an insufflator into a chamber having a means for heating the gas to a temperature within a predetermined range and a means for humidifying the gas and being disposed immediately adjacent to the patient, wherein the chamber is in flow communication with and immediately adjacent to a means for delivering the gas to the interior of the patient;
    b) sensing the temperature of the gas as it exits the chamber to determine if it is within the predetermined range; and
    c) actuating the heating means if the temperature of the gas is without the predetermined range;
    d) humidifying the gas within the chamber; and
    e) flowing the gas into the delivering means such that the gas enters the patient humidified and having a temperature within 2° C. of the predetermined temperature and thus providing the gas.

12. The method of claim 11, wherein the heating means and the humidifying means heat and humidify the gas simultaneously.

13. The method of claim 12, further comprising the step of filtering the gas as it is heated and humidified.

14. The method of claim 13, further comprising the step of filtering the gas a second time after it is heated and humidified.

15. The method of claim 11, wherein the heating means is controlled by a power source comprising a self-contained battery of voltage in the range of about 1.6–3.0.

* * * * *

(12) EX PARTE REEXAMINATION CERTIFICATE (7783rd)
United States Patent
Ott et al.

(10) Number: US 5,411,474 C1
(45) Certificate Issued: Oct. 5, 2010

(54) METHOD AND APPARATUS FOR CONDITIONING INSUFFLATION GAS FOR LAPAROSCOPIC SURGERY

(75) Inventors: Douglas E. Ott, Macon, GA (US); John F. Schaefer, Macon, GA (US); Robert I. Gray, Macon, GA (US)

(73) Assignee: Lexion Medical, LLC, St. Paul, MN (US)

Reexamination Request:
No. 90/010,561, Jul. 16, 2009

Reexamination Certificate for:
Patent No.: 5,411,474
Issued: May 2, 1995
Appl. No.: 08/091,658
Filed: Jul. 14, 1993

(51) Int. Cl.
*A61M 37/00* (2006.01)

(52) U.S. Cl. .................. 604/26; 604/506; 604/23; 604/560

(58) Field of Classification Search .................. None
See application file for complete search history.

(56) References Cited

U.S. PATENT DOCUMENTS

| | | |
|---|---|---|
| 2,408,136 A | 9/1946 | Fox |
| 3,582,717 A | 6/1971 | Perlaky ............... 317/148.5 B |
| 4,092,635 A | 5/1978 | Warner .................. 340/235 |
| 4,121,583 A | 10/1978 | Chen |
| 4,215,681 A | 8/1980 | Zalkin et al. .......... 128/204.21 |
| 4,225,542 A | 9/1980 | Wall et al. ............... 261/142 |
| 4,230,116 A | 10/1980 | Watson .................. 128/303 A |
| 4,360,017 A | 11/1982 | Barlett .................. 128/202.28 |
| 4,369,777 A | 1/1983 | Lwoff et al. |
| 4,401,114 A | 8/1983 | Lwoff et al. ........... 128/200.14 |
| 4,621,632 A | 11/1986 | Bartels et al. .......... 128/203.27 |
| 4,674,494 A | 6/1987 | Wiencek ................ 128/203.16 |
| 4,686,974 A | 8/1987 | Sato et al. |
| 4,714,078 A | 12/1987 | Paluch .................. 128/203.17 |
| 4,770,168 A | 9/1988 | Rusz et al. ............. 128/203.12 |
| 4,921,642 A | 5/1990 | LaTorraca ................. 261/142 |
| 5,006,109 A | 4/1991 | Douglas et al. |
| 5,013,294 A | 5/1991 | Baier ..................... 604/26 |
| 5,042,468 A | 8/1991 | Lambert et al. ........ 128/200.26 |
| 5,062,145 A | 10/1991 | Zwaan et al. |
| 5,195,515 A | 3/1993 | Levine ................. 128/203.26 |
| 5,349,946 A | 9/1994 | McComb |
| 5,383,447 A | 1/1995 | Lang ..................... 128/201.13 |
| 5,399,159 A | 3/1995 | Chin et al. ................ 604/26 |
| 5,482,031 A | 1/1996 | Lambert ................ 128/203.12 |
| 5,599,297 A | 2/1997 | Chin et al. ................ 604/26 |
| 6,068,609 A | 5/2000 | Ott et al. .................. 604/26 |
| 6,814,714 B1 | 11/2004 | Novak et al. ............. 604/114 |
| 7,066,902 B1 | 6/2006 | Ott et al. .................. 604/23 |
| 2005/0107766 A1 | 5/2005 | Ott et al. .................. 604/500 |
| 2005/0107767 A1 | 5/2005 | Ott et al. .................. 604/500 |
| 2005/0113795 A1 | 5/2005 | Ott et al. .................. 604/500 |
| 2005/0113797 A1 | 5/2005 | Ott et al. .................. 604/506 |

FOREIGN PATENT DOCUMENTS

AU        74564/74        4/1976

(Continued)

OTHER PUBLICATIONS

*Leitfaden und Atlas der Laparoskopie*, W. Siede and H. Schneider, J.F. Lehmanns Verlag München, 1962 (with partial translation), 6 pages.

*The persufflator: an insufflation device for laparoscopy and especially for $CO_2$–laser endoscopic surgery*, P. Koninckx and E. Vandermeersh, 1991, 3 pages.

(Continued)

*Primary Examiner*—Jeffrey R. Jastrzab (57) ABSTRACT

The present invention provides an apparatus for treating gas prior to its use in a medical procedure comprising a housing that receives gas from an insufflator, a chamber within the housing having a humidification means, a heating means disposed within the humidification means, a filtering means within the humidification means, a means for sensing the temperature of the heated and humidified gas, and a controlling means connected to the sensing means to maintain the temperature of the gas to a predetermined temperature. Additionally provided are methods of providing heated, humidified and filtered gas to a patient at a predetermined temperature.

FOREIGN PATENT DOCUMENTS

| | | |
|---|---|---|
| DE | 2834622 A1 | 2/1979 |
| DE | 2810325 A1 | 9/1979 |
| DE | 3139135 | 10/1982 |
| DE | 3430541 | 7/1985 |
| DE | 3615611 C2 | 11/1986 |
| DE | 3932766 A1 | 4/1990 |
| DE | 3927594 A1 | 6/1990 |
| EP | 0 169151 B1 | 1/1986 |
| EP | 0 533644 B1 | 9/1992 |
| EP | 0 569 241 A2 | 6/1993 |
| EP | 0 387 220 B2 | 1/1995 |
| EP | 1 386 629 A2 | 11/1995 |
| EP | 0 827 417 B1 | 11/1998 |
| WO | WO 91/19527 | 12/1991 |
| WO | WO 94/28952 | 12/1994 |

OTHER PUBLICATIONS

Mohamed Hamza, MD, et al., "Optimal Warming Technique for Major Laparoscopic Surgery: Forced Air Warming or Warmed and Humidified Insufflation Gas", Reference: Anesth. Analg. 96: S121; 1 page, date unknown.

Todd M. Beste, M.D., et al., "Humidified Compared With Dry, Heated Carbon Dioxide at Laparoscopy to Reduce Pain", Obstetrics & Gynecology, vol. 107, No. 2, Part 1; pp. 263–268, Feb. 2006.

J. de Csepel et al., Letter to the Editor: "Heating and humidifying carbon dioxide is indicated", Surg Endosc 21; pp. 340–341, 2007.

K. Slim, et al., "Effect of $CO_2$ gas warming on pain after laparoscopic surgery", Surgical Endoscopy 13; pp. 1110–1114, 1999.

V.L. Wills, et al., "A randomized controlled trial assessing the effect of heated carbon dioxide for insufflation on pain and recovery after laparoscopic fundoplication", Surg Endosc 15; pp. 166–170, 2001.

Yuanfei Peng, Ph.D., et al., "Heated and Humidified $CO_2$ Prevents Hypothermia, Peritoneal Injury, and Intra–Abdominal Adhesions During Prolonged Laparoscopic Insufflations", Journal of Surgical Research 151; pp. 40–47, 2009.

Benjamin E. Schneider, MD, Mohamed A. Hamza, MD, Alex Recart, MD, P.F. White, MD, PhD, Tunde Ogunnaike, MD, D. Provost, MD, D. Jones, MD, "Role of Heated and Humidified Intraperitoneal Gases Using an Insuflow® Device During Laparoscopic Roux–En–Y Surgery—Effect on Temperature, Post–Operative Pain, and Recovery", Sages 200, Abstract #495, Poser #59, 2 pgs., 2003.

Semm K, Arp WD, Trappe M. Kube D, "Pain reduction after pelvi/–laparoscopic interventions by insufflation of CO2 gas at body temperature (Flow–Therme)", National Library of Medicine; 1 page, May 1994.

The Journal of the American Association of Gynecologic Laparoscopists, vol. 6, No. 3 Supplement; p. S43, Aug. 1999.

T. Sammour, A. Kahokehr, A.G. Hill, "Meta–analysis of the effect of warm humidified insufflation on pain after laparoscopy", British Journal of Surgery 95; pp. 950–956, 2008.

Richard Benavides, MD, A. Wong, MD, Hoang Nguyen, MD, "Improved Outcomes for Lap–Banding Using the Insuflow® Device Compared with Heated–Only Gas", Journal of the Society of Laparoendoscopic Surgeons 13; pp. 302–305, 2009.

Douglas E. Ott, M.D., MBA, "Laparoscopy and Tribology: The Effect of Laparoscoic Gas on Peritoneal Fluid", The Journal of the American Association of Gynecologic Laparoscopists; pp. 117–123, Feb. 2001.

Muhammad Shafique Sajid, FRCS, Ali Sameer Mallick, MBBS, Jasmin Rimpel, MBBS, Syed Awais Bokari, MBBS, Elizabeth Cheek, MSc, and Mirza Khurrum Baig, FRCS, "Effect of Heated and Humidified Carbon Dioxide on Patients After Laparoscopic Procedures, a Meta–analysis", Surg Laparosc Endosc Percutan Tech, vol. 18, No. 6; pp. 539–546, Dec. 2008.

S.S. Davis, D.J. Mikami, M. Newlin, B.J. Needleman, M.S. Barrett, R. Fries, T. Larson, J. Dundon, M.I. Goldblatt, W.S. Melvin, "Heating and humidifying of carbon dioxide during pneumoperitoneum is not indicated", Surg. Endosc (2006); pp. 153–158, Dec. 2005.

Oscar Almeida, "Awake Micro–Laparoscopy with the Insuflow® Device", Journal of the Society of Laparoendoscopic Surgeons 6:; (4 pgs), Aug. 2002.

Larry A. Demco, MD, "Painless Laparoscopy?", Laparoscopy and SLS Report, (2 pgs), 2002.

David R. Farley, MD, S. M. Greenlee, RN, D. R. Larson, MS, J. R. Harrington, MA, "Double–blind, Prospective, Randomized Study of Warmed, Humidified Carbon Dioxide-Insufflation vs. Standard Carbon Dioxide for Patients Undergoing Laparoscopic Cholecystectomy", Arch Surg/ vol. 139; pp. 739–744, Jul. 2004.

M. Korell, M.D., F. Schmaus, M.D., T. Strowitzki, M.D., S.G. Schneeweiss, M.D., and H. Hepp, M.D., "Pain Intensity Following Laparoscopy", Surgical Laparoscopy & Endoscopy, vol. 6, No. 5, pp. 375–379, 1996.

Larry Demco, M.D., "Effect of Heating and Humidifying Gas on Patients Undergoing Awake Laparoscopy", The Journal of the American Association of Gynecologic Laparoscopists, vol. 8, No. 2; pp. 247–251, May 2001.

Raja Kandaswamy, MD, K. Gillingham, J. Harmon, M. Asolati, "Decreased Incidence of Hypothermia and Peritoneal Irritation in Laparoscopic Donor Nephrectomy Using A Filter–Hydrator–Heating Device (Insuflow®)", Sages 2003 Poster Program—Basic Science—PO69, 1 pg, 2003.

Mohamed Hamza, MD, A. Recart, MD, P. F. White, MD, Tunde Ogunnaike, MD, Benjamin Schneider, MD, D. Provost, MD, D. Jones, MD, "Role of Heated and Humidified Intraperitoneal Gases Using an Insuflow® Device During Laparoscopic Roux–En–Y Surgery—Effect on Temperature, Post–Operative Pain, and Recovery", IARS 2003—Abstract #S121; 2 pages, 2003.

Mohamed A. Hamza, MD, Benjamin E. Schneider, MD, P. F. White, MD, PhD, Alejandro Recart, MD, Leonard Villegas, MD, Babatunde Ogunnaike, MD, D. Provost, MD, and D. Jones, MD, "Heated and Humidified Insufflation During Laparoscopic Gastric Bypass Surgery: Effect on Temperature, Postoperative Pain, and Recovery Outcomes", Journal of Laparoendoscopic & Advanced Surgical Techniques, vol. 15, No. 1; pp. 6–12, 2005.

Ott DE, Reich H, Love B, McCorvey R, Toledo A, Liu CY, Syed R, Kumar K, "Reduction of laparoscopic–induced hypothermia, postoperative pain and recovery room length of stay by preconditioning gas with the Insuflow device: a prospective randomized controlled multi–center study", JSLS 1998 Oct.–Dec.2(4); pp. 321–329, 10 pgs, 1998.

Douglas E. Ott, MD, MBA, "Reduced Peritoneal Inflammation Using Wet Gas Compared to Cold Dry Gas as Measured by C–reactive Protein and Interleukin–6", 1 page, date unknown.

Douglas E. Ott, MD, "Desertification of the Peritoneum by Thin–Film Evaporation During Laparoscopy", JSLS (2003); pp. 189–195.

DM Wiseman, "Humidity and Temperature Insufflation Gas on Intact Peritoneum", Abstracts of the Global Congress of Gynecological Endoscopy 31st Annual Meeting of the American Association of Gynecologic Laparoscopists, 3 pgs, Nov. 2002.

Abstracts of the Global Congress of Gynecological Endoscopy 31st Annual Meeting of the American Association of Gynecologic Laparoscopists, 2 pages, Nov. 2002.

Bessell, Jr., Karatassas, A., Patteson Jr., Jamieson G.G., Maddern G.J., "Hypothermia induced by laparoscopic insufflation. A randomized study in a pig model.", Dept. of Surgery, Univ. of Adelaide, Queen Elizabeth Hospital, Australia, PubMed medline query, (1 pg), Jul. 1995.

J.R. Bessell and G.J. Maddern, "Influence of Gas Temperature During Laparoscopic Procedures", Pathophysiology of Pneumo–peritoneum, R. Rosenthal, et al., Springer; pp. 18–27, 1998.

S. Saad, I. Minor, T. Mohri, M. Gagelschmidt, "The clinical impact of warmed insufflation carbon dioxide gas for laparoscopic cholecystectomy", Surgical Endoscopy, Springer; pp. 787–790, 2000.

W.G. Mouton, J.R, Bessell, K.T. Otten, G.J. Maddern., "Pain after laparoscopy", Review Article, Surg Endosc (1999) 13: pp. 445–448.

"Hypothermia—A potential risk of $CO_2$ insufflation?", Editorial, Surg Endosc (1999) 13: 99–100, Springer–Verlag; (2 pgs).

Certificate of Registration, Register of Copyrights, Copyright Office for Insuflow Brochure (11 pgs), May 3, 2004.

M.A. Raymond, et al., "Feasibility of Therapeutic Pneumoperitoneum in a Large Animal Model Using a Microvaporisator", Surgical Endoscopy: Ultrasound and Interventional Techniques; pp. 51–55, 2000.

W. Karrer, "Pillars of therapy of chronic obstructive bronchitis", Schweiz Rundsch Med Prax.; 78(6); 121–5, Germany; (1 pg), Feb. 7, 1989.

Cook Medical Technology Technological Observer, Cook Australia, A delaid trial demonstrates significant reduction of post–operative pain when using heated and humidied $CO_2$, and "New features on the LINS–1000 enhance performance"; pp. 1–6, Jan. 1998.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 11 and 12 is confirmed.

New claims 16-76 are added and determined to be patentable.

Claims 1-10 and 13-15 were not reexamined.

16. The method of claim 11, wherein the insufflator includes a first control for adjusting the pressure of the gas and a second control for adjusting the flow rate of the gas.

17. The method of claim 11, wherein the gas is carbon dioxide.

18. The method of claim 11, wherein the endoscopic procedure is a laparoscopic procedure.

19. The method of claim 11, wherein the means for delivering comprises a trocar.

20. The method of claim 11, wherein the means for delivering comprises a needle.

21. The method of claim 11, wherein the step of sensing the temperature of the gas as it exits the chamber further comprises sensing the temperature of the gas after it has been humidified.

22. The method of claim 11, wherein the step of sensing the termperature of the gas as it exits the chamber further comprises sensing the temperature of the gas using at least one temperature sensor.

23. The method of claim 22, wherein the at least one temperature sensor comprises a thermistor.

24. The method of claim 11, wherein the step of sensing the temperature as it exits the chamber further comprises generating a signal, the method further comprising receiving the signal with a feedback control circuit that is operable to perform the actuating step.

25. The method of claim 22, wherein the at least one temperature sensor is located adjacent an exit port of the chamber.

26. The method of claim 22, wherein the at least one temperature sensor detects the temperature of the gas at the exit end of the chamber.

27. The method of claim 22, wherein the at least one temperature sensor's electrical resistance changes with temperature.

28. The method of claim 11, wherein the humidification means is in the path of travel of gas through the chamber.

29. The method of claim 11, wherein the humidification means comprises a volume of water.

30. The method of claim 11, wherein the humidification means comprises a volume of water between two gas permeable membranes within the chamber.

31. The method of claim 11, wherein the humidification means comprises a water containing bed.

32. The method of claim 11, wherein the humidification means comprises a porous bed of entrapped water.

33. The method of claim 11, wherein the humidification means comprises a water retaining material infused with water.

34. The method of claim 11, wherein the gas is humidified to a relative humidity between 85 and 98%.

35. The method of claim 11, wherein the gas is humidified to a relative humidity level of at least 75%.

36. The method of claim 11, wherein the gas is humidified to a relative humidity level of at least 85%.

37. The method of claim 11, wherein the gas is humidified to a relative humidity level of at least 60%.

38. The method of claim 11, wherein the chamber is within a heater/humidifier that can be held in a person's hand.

39. The method of claim 11, wherein the chamber is within a disposable heater/humidifier.

40. The method of claim 11, wherein the means for heating comprises an electrical resistance heater.

41. The method of claim 11, wherein the means for heating is disposed within the means for humidification.

42. The method of claim 11, wherein the means for heating is disposed within a volume of water.

43. The method of claim 11 wherein the means for heating is disposed around a volume of water.

44. The method of claim 11, wherein the chamber is within ten inches of the patient.

45. The method of claim 11, wherein the chamber is within ten centimeters of the patient.

46. The method of claim 11, wherein the insufflator receives gas from a cylinder.

47. The method of claim 11, wherein the predetermined temperature is a single temperature point selected from 36-38 degrees Celsius.

48. The method of claim 11, further comprising filtering the heated and humidified gas.

49. The method of claim 18, wherein the chamber is within ten inches of the means for delivering and wherein the means for delivering comprises a trocar or needle.

50. The method of claim 49, wherein the gas is carbon dioxide.

51. The method of claim 50, wherein the humidification means comprises a water retaining material infused with water.

52. The method of claim 49, wherein the gas is humidified to a relative humidity between 85 and 98%.

53. The method of claim 49, wherein the gas is humidified to a relative humidity level of at least 75%.

54. The method of claim 49, wherein the gas is humidified to a relative humidity level of at least 85%.

55. The method of claim 49, wherein the gas is humidified to a relative humidity level of at last 60%.

56. The method of claim 50, wherein the humidification means comprises a porous bed of entrapped water.

57. The method of claim 50, wherein the chamber is within a heater/humidifier that can be held in a person's hand.

58. The method of claim 50, wherein the means for heating comprises an electrical resistance heater.

59. The method of claim 50 wherein the means for heating is disposed within the means for humidification.

60. A method of providing heated, humidified gas into a patient for an endoscopic procedure that is a laparoscopic procedure comprising the steps of:

a) directing pressure- and volumetric flow rate-controlled carbon dioxide gas, received from an insufflator into a chamber having a means for heating the gas to a temperature within a predetermined range and a means for humidifying the gas and being disposed immediately adjacent to the patient, wherein immediately adjacent means within about zero to ten inches of the patient, wherein the chamber is in flow communication with and immediately adjacent to a means for delivering the gas to the interior of the patient, wherein immediately adjacent means within about zero to ten inches of the means for delivering, wherein the means for delivering is a trocar or needle inserted into the peritoneal cavity of the patient;

b) sensing the temperature of the gas as it exits the chamber to determine if it is within the predetermined range; and c) actuating the heating means if the temperature of the gas is without the predetermined range;

d) humidifying the gas within the chamber; and e) flowing the gas into the delivering means such that the gas enters the patient humidified and having a temperature within 2° C. of the predetermined temperature and thus providing the gas.

61. The method of claim 60, wherein the step of sensing the temperature of the gas as it exits the chamber further comprises sensing the temperature of the gas using at least one temperature sensor.

62. The method of claim 60, wherein the step of sensing the temperature of the gas as it exits the chamber further comprises sensing the temperature of the gas after it has been humidified.

63. The method of claim 60, wherein the humidification means is in the path of travel of gas through the chamber.

64. The method of claim 60, wherein the humidification means comprises a volume of water.

65. The method of claim 60, wherein the humidification means comprises a porous bed of entrapped water.

66. The method of claim 60, wherein the humidification means comprises a water retaining material infused with water.

67. The method of claim 66, wherein the gas is humidified to a relative humidity level of at least 75%.

68. The method of claim 66, wherein the gas is humidified to a relative humidity level of at least 60%.

69. The method of claim 66, wherein the gas is humidified to a relative humidity level of at least 85%.

70. The method of claim 66, wherein the chamber is within a heater/humidifer that can be held in a person's hand.

71. The method of claim 66, wherein the predetermined temperature is a single temperature point between 36-38 degrees Celsius.

72. The method of claim 66, wherein the means for heating comprises an electrical resistance heater.

73. The method of claim 66, wherein the gas is humidified to a relative humidity level of at least 75% and wherein the predetermined temperature is a single temperature point between 36-36 degrees Celsius.

74. The method of claim 72, wherein the step of sensing the temperature as it exits the chamber further comprises generating a signal, the method further comprising receiving the signal with a feedback control circuit that is operable to perform the actuating step.

75. The method of claim 72, wherein the means for heating is disposed within the means for humidification.

76. The method of claim 60, wherein a temperature controller generates a reference voltage and wherein it is determined if the temperature is within the predetermined range by comparing the reference voltage with a voltage generated by the temperature sensor.

\* \* \* \* \*